(12) United States Patent
Brucker et al.

(10) Patent No.: US 6,695,877 B2
(45) Date of Patent: Feb. 24, 2004

(54) BIFURCATED STENT

(75) Inventors: Gregory G. Brucker, Minneapolis, MN (US); Todd Hall, Goshen, KY (US); Enrique Malaret, Plymouth, MN (US); David Byrd, Louisville, KY (US); Gerald Hubbs, Louisville, KY (US); Gregory Furnish, Louisville, KY (US); Josh Barber, Louisville, KY (US); Indaka Gunasekara, Louisville, KY (US); Benjamin Morris, Louisville, KY (US); Valerie Futral, Louisville, KY (US); Sava A. Chernomordik, Louisville, KY (US); William C. Mers Kelly, Crestwood, KY (US); William A. Reuss, Jr., Louisville, KY (US); Simon Furnish, New York City, NY (US); Michael W. Wilson, LaGrage, KY (US); Hacene Bouadi, Palo Alto, CA (US); John C. Muskivitch, Cupertino, CA (US); Matthew L. Pease, Mountain View, CA (US); David A. Rahdert, San Francisco, CA (US); Travis Rowe, Fremont, CA (US); Gregory M. Ruhf, Cupertino, CA (US); Brandon G. Walsh, Livermore, CA (US); Claude Vidal, Santa Barbara, CA (US); Thomas Banks, Santa Barbara, CA (US); Russ Redmond, Goleta, CA (US)

(73) Assignee: SciMed Life Systems, Maple Grove, MN (US)

( * ) Notice: Subject to any disclaimer, the term of this patent is extended or adjusted under 35 U.S.C. 154(b) by 0 days.

(21) Appl. No.: 10/084,766

(22) Filed: Feb. 26, 2002

(65) Prior Publication Data

US 2002/0173840 A1 Nov. 21, 2002

Related U.S. Application Data

(60) Provisional application No. 60/271,506, filed on Feb. 26, 2001, provisional application No. 60/271,595, filed on Feb. 26, 2001, and provisional application No. 60/271,602, filed on Feb. 26, 2001.

(51) Int. Cl.[7] ............................................. A61F 2/06
(52) U.S. Cl. ..................................... 623/1.16; 623/1.35
(58) Field of Search ............................. 623/1.16, 1.35, 623/1.13

(56) References Cited

U.S. PATENT DOCUMENTS

| 1,861,769 A | 6/1932 | Wappler |
| 2,845,959 A | 8/1958 | Sidebotham |

(List continued on next page.)

FOREIGN PATENT DOCUMENTS

| CA | 2220864 | 7/1999 | ............. A61F/2/06 |
| DE | 29701758 | 5/1997 | ............ A61M/29/00 |

(List continued on next page.)

*Primary Examiner*—Corrine McDermott
*Assistant Examiner*—Thomas Sweet
(74) *Attorney, Agent, or Firm*—Vidas, Arrett & Steinkraus, P.A.

(57) ABSTRACT

A bifurcated stent comprises a first stent section and a second stent section. Each stent section is expandable from a predeployed state to a deployed state independently from one another. The second stent section having an end engaged to a receiving region of the first stent section. In the deployed state the first stent section defines a primary flow path and the second stent section defines a secondary flow path in fluid communication with the first flow path. At least a portion of one or both the first stent section and second stent section is constructed from a wire member.

23 Claims, 13 Drawing Sheets

U.S. PATENT DOCUMENTS

| | | | |
|---|---|---|---|
| 4,413,989 A | 11/1983 | Schjeldahl et al. | 604/96 |
| 4,454,887 A | 6/1984 | Kruger | 128/772 |
| 4,730,616 A | 3/1988 | Frisbie et al. | 604/53 |
| 4,769,005 A | 9/1988 | Ginsburg et al. | 604/53 |
| 4,774,949 A | 10/1988 | Fogarty | 128/348.1 |
| 4,896,670 A | 1/1990 | Crittenden | 606/194 |
| 4,905,667 A | 3/1990 | Foerster et al. | 128/4 |
| 4,957,508 A | 9/1990 | Kaneko et al. | 632/12 |
| 4,983,166 A | 1/1991 | Yamawaki | 604/96 |
| 4,994,071 A | 2/1991 | MacGregor | 606/194 |
| 5,156,620 A | 10/1992 | Pigott | 623/1 |
| 5,219,355 A | 6/1993 | Parodi et al. | 606/191 |
| 5,320,605 A | 6/1994 | Sahota | 604/101 |
| 5,342,387 A | 8/1994 | Summers | 606/198 |
| 5,443,497 A | 8/1995 | Venbrux | 623/1 |
| 5,575,771 A | 11/1996 | Walinsky | 604/96 |
| 5,599,300 A | 2/1997 | Weaver et al. | 604/54 |
| 5,607,444 A | 3/1997 | Lam | 606/194 |
| 5,613,980 A | 3/1997 | Chauhan | 606/194 |
| 5,617,878 A | 4/1997 | Taheri | 128/898 |
| 5,632,762 A | 5/1997 | Myler | 606/194 |
| 5,632,763 A | 5/1997 | Glastra | 606/194 |
| 5,639,278 A | 6/1997 | Dereume et al. | 623/1 |
| 5,669,924 A | 9/1997 | Shaknovich | 606/108 |
| 5,672,153 A | 9/1997 | Lax et al. | 604/22 |
| 5,683,450 A | 11/1997 | Goicoechea et al. | 623/1 |
| 5,693,086 A | 12/1997 | Goicoechea et al. | 623/1 |
| 5,697,971 A | 12/1997 | Fischell et al. | 623/1 |
| 5,720,735 A | 2/1998 | Dorros | 604/284 |
| 5,749,825 A | 5/1998 | Fischell et al. | 600/3 |
| 5,749,890 A | 5/1998 | Shaknovich | 606/198 |
| 5,755,734 A | 5/1998 | Richter et al. | 606/194 |
| 5,755,735 A | 5/1998 | Richter et al. | 606/194 |
| 5,755,770 A | 5/1998 | Ravenscroft | 623/1 |
| 5,755,771 A | 5/1998 | Penn et al. | 623/1 |
| 5,755,772 A | 5/1998 | Evans et al. | 623/1 |
| 5,755,773 A | 5/1998 | Evans et al. | 623/1 |
| 5,755,778 A | 5/1998 | Kleshinski | 623/1 |
| 5,776,101 A | 7/1998 | Goy | 604/104 |
| 5,782,906 A | 7/1998 | Marshall et al. | 604/194 |
| 5,800,508 A | 9/1998 | Goicoechea et al. | 623/1 |
| 5,800,520 A | 9/1998 | Fogarty et al. | 623/1 |
| 5,827,320 A | 10/1998 | Richter et al. | 606/194 |
| 5,855,600 A | 1/1999 | Alt | 623/1 |
| 5,868,777 A | 2/1999 | Lam | 606/194 |
| 5,893,887 A | 4/1999 | Jayaraman | 623/1 |
| 5,906,640 A | 5/1999 | Penn et al. | 623/1 |
| 5,916,263 A | 6/1999 | Goicoechea et al. | 623/1 |
| 5,921,995 A | 7/1999 | Kleshinski | 606/153 |
| 5,938,696 A | 8/1999 | Goicoechea et al. | 623/1 |
| 5,961,490 A | 10/1999 | Adams | 604/96 |
| 5,961,548 A | 10/1999 | Shmulewitz | 623/1 |
| 5,968,089 A | 10/1999 | Krajicek | 623/1 |
| 5,972,017 A | 10/1999 | Berg et al. | 606/198 |
| 5,984,955 A | 11/1999 | Wisselink | 623/1 |
| 5,993,481 A | 11/1999 | Marcade et al. | 623/1 |
| 6,013,054 A | 1/2000 | Jiun Yan | 604/96 |
| 6,016,810 A | 1/2000 | Ravenscroft | 128/898 |
| 6,017,324 A | 1/2000 | Tu et al. | 604/96 |
| 6,017,363 A | 1/2000 | Hojeibane | 623/1 |
| 6,030,414 A | 2/2000 | Taheri | 623/1 |
| 6,033,434 A | 3/2000 | Borghi | 623/1 |
| 6,033,435 A | 3/2000 | Penn et al. | 623/1 |
| 6,036,723 A * | 3/2000 | Anidjar et al. | 623/1.13 |
| 6,039,758 A | 3/2000 | Quiachon et al. | 623/1 |
| 6,045,557 A | 4/2000 | White et al. | 606/108 |
| 6,048,360 A | 4/2000 | Khosravi et al. | 623/1 |
| 6,048,361 A | 4/2000 | Von Oepen | 623/1 |
| 6,051,020 A | 4/2000 | Goicoechea et al. | 623/1 |
| 6,056,722 A | 5/2000 | Jayaraman | 604/102 |
| 6,056,775 A | 5/2000 | Borghi et al. | 623/1.16 |
| 6,059,824 A | 5/2000 | Taheri | 623/1 |
| 6,068,655 A | 5/2000 | Seguin et al. | 623/1 |
| 6,086,611 A | 7/2000 | Duffy et al. | 623/1 |
| 6,090,133 A | 7/2000 | Richter et al. | 623/1 |
| 6,093,203 A | 7/2000 | Uflacker | 612/1.12 |
| 6,096,073 A | 8/2000 | Webster et al. | 623/1.16 |
| 6,099,558 A | 8/2000 | White et al. | 623/1.16 |
| 6,099,560 A | 8/2000 | Penn et al. | 623/1.35 |
| 6,102,938 A | 8/2000 | Evans et al. | 623/1 |
| 6,117,117 A | 9/2000 | Mauch | 604/284 |
| 6,117,156 A | 9/2000 | Richter et al. | 606/194 |
| 6,129,738 A | 10/2000 | Lashinski et al. | 606/194 |
| 6,129,754 A | 10/2000 | Kanesaka et al. | 623/1 |
| 6,132,459 A | 10/2000 | Piplani et al. | 623/1.13 |
| 6,142,973 A | 11/2000 | Carleton et al. | 604/96 |
| 6,143,002 A | 11/2000 | Vietmeier | 606/108 |
| 6,159,238 A | 12/2000 | Killion et al. | 623/1.11 |
| 6,165,195 A | 12/2000 | Wilson et al. | 606/194 |
| 6,165,213 A | 12/2000 | Goicoechea et al. | 623/1.34 |
| 6,168,621 B1 | 1/2001 | Vrba | 623/1.2 |
| 6,183,509 B1 | 2/2001 | Dibie | 623/1.35 |
| 6,197,046 B1 | 3/2001 | Piplani et al. | 623/1.11 |
| 6,197,049 B1 | 3/2001 | Shaolian et al. | 623/1.35 |
| 6,210,380 B1 | 4/2001 | Mauch | 604/284 |
| 6,210,429 B1 | 4/2001 | Vardi et al. | 623/1 |
| 6,210,431 B1 | 4/2001 | Power | 623/1.11 |
| 6,210,433 B1 | 4/2001 | Larre | 623/1.15 |
| 6,217,527 B1 | 4/2001 | Selmon et al. | 600/285 |
| 6,221,080 B1 | 4/2001 | Power | 606/108 |
| 6,221,090 B1 | 4/2001 | Wilson | 606/194 |
| 6,221,098 B1 | 4/2001 | Wilson et al. | 623/1.11 |
| 6,231,563 B1 | 5/2001 | White et al. | 604/523 |
| 6,231,598 B1 | 5/2001 | Berry et al. | 623/1.15 |
| 6,238,430 B1 | 5/2001 | Klumb et al. | 623/1.11 |
| 6,248,122 B1 | 6/2001 | Klumb et al. | 606/194 |
| 6,251,133 B1 | 6/2001 | Richter et al. | 623/1.16 |
| 6,254,593 B1 | 7/2001 | Wilson | 606/1.11 |
| 6,258,073 B1 | 7/2001 | Mauch | 604/284 |
| 6,258,115 B1 | 7/2001 | Dubrul | 606/200 |
| 6,258,116 B1 | 7/2001 | Hojeibane | 623/1.16 |
| 6,261,273 B1 | 7/2001 | Ruiz | 604/284 |
| 6,261,305 B1 | 7/2001 | Marotta et al. | 606/200 |
| 6,261,316 B1 | 7/2001 | Shaolian et al. | 623/1.11 |
| 6,264,662 B1 | 7/2001 | Lauterjung | 606/108 |
| 6,264,686 B1 | 7/2001 | Rieu et al. | 623/1.16 |
| 6,273,909 B1 | 8/2001 | Kugler et al. | 623/1.13 |
| 6,287,277 B1 | 9/2001 | Yan | 604/96.01 |
| 6,290,673 B1 | 9/2001 | Shanley | 604/102 |
| 6,302,906 B1 | 10/2001 | Goicoechea et al. | 623/1.11 |
| 6,302,908 B1 | 10/2001 | Parodi | 623/1.31 |
| 6,306,164 B1 | 10/2001 | Kujawski | 623/1.25 |
| 6,312,461 B1 | 11/2001 | Unsworth et al. | 623/1.19 |
| 6,319,278 B1 | 11/2001 | Quinn | 623/1.13 |
| 6,322,587 B1 | 11/2001 | Quiachon et al. | 623/1.23 |
| 6,325,819 B1 | 12/2001 | Pavcnik et al. | 623/1.11 |
| 6,325,822 B1 | 12/2001 | Chouinard et al. | 623/1.15 |
| 6,325,823 B1 * | 12/2001 | Horzewski et al. | 623/1.16 |
| 6,325,826 B1 | 12/2001 | Vardi et al. | 623/1.35 |
| 6,334,864 B1 | 1/2002 | Amplatz et al. | 606/200 |
| 6,383,213 B2 | 5/2002 | Wilson et al. | 623/1.11 |
| 6,387,120 B2 | 5/2002 | Wilson et al. | 623/1.11 |
| 2001/0002443 A1 | 5/2001 | Parodi | |
| 2001/0002927 A1 | 6/2001 | Detampel | |
| 2001/0002943 A1 | 6/2001 | Nagayama et al. | |
| 2001/0003161 A1 | 6/2001 | Vardi et al. | |
| 2001/0004705 A1 | 6/2001 | Killion et al. | |
| 2001/0004706 A1 | 6/2001 | Hojeibane | |
| 2001/0004707 A1 | 6/2001 | Dereume et al. | |
| 2001/0004823 A1 | 6/2001 | Cronim et al. | |
| 2001/0007954 A1 | 7/2001 | Shaolian et al. | |

| | | | |
|---|---|---|---|
| 2001/0016766 A1 | 8/2001 | Vardi et al. | |
| 2001/0016767 A1 | 8/2001 | Wilson et al. | |
| 2001/0016768 A1 | 8/2001 | Wilson et al. | |
| 2001/0020173 A1 | 9/2001 | Klumb et al. | |
| 2001/0020184 A1 | 9/2001 | Dehdashtian | |
| 2001/0025195 A1 | 9/2001 | Sholian | |
| 2001/0027291 A1 | 10/2001 | Shanley | |
| 2001/0029396 A1 | 10/2001 | Wilson et al. | |
| 2002/0120327 A1 * | 8/2002 | Cox et al. | 623/1.16 |

FOREIGN PATENT DOCUMENTS

| | | | |
|---|---|---|---|
| EP | 0479730 | 10/1991 | A61M/29/02 |
| EP | 0686379 | 12/1995 | A61F/2/06 |
| EP | 0751752 | 1/1997 | A61F/2/06 |
| EP | 0479557 | 7/1997 | A61F/2/06 |
| EP | 0783873 | 7/1997 | A61F/2/06 |
| EP | 0804907 | 11/1997 | A61F/2/06 |
| EP | 0647148 | 12/1998 | A61M/29/00 |
| EP | 0880949 | 12/1998 | A61F/2/06 |
| EP | 0897700 | 2/1999 | A61F/2/06 |
| EP | 0904745 | 3/1999 | A61F/2/06 |
| EP | 0937442 | 8/1999 | A61F/2/06 |
| EP | 0 947 180 | 10/1999 | |
| EP | 0347023 | 12/1999 | A61M/25/00 |
| EP | 1031329 | 8/2000 | A61F/2/06 |
| EP | 1031330 | 8/2000 | A61F/2/06 |
| EP | 0883384 | 12/2000 | A61F/2/06 |
| EP | 0862392 | 8/2001 | A61F/2/06 |
| EP | 0808140 | 12/2001 | A61F/2/06 |
| FR | 2 678 508 | 7/1991 | |
| FR | 2678508 | 7/1991 | A61F/2/06 |
| FR | 2740346 | 10/1995 | A61F/25/10 |
| FR | 2756173 | 11/1996 | A61F/2/06 |
| FR | 2760351 | 3/1997 | A61F/2/06 |
| GB | 2337002 | 5/1998 | A61F/2/06 |
| WO | 9510442 | 4/1995 | B62D/21/02 |
| WO | 9521592 | 8/1995 | A61F/2/06 |
| WO | 9634580 | 11/1996 | A61F/2/06 |
| WO | 9641592 | 12/1996 | A61F/2/06 |
| WO | 9707752 | 3/1997 | A61F/2/06 |
| WO | 9715346 | 5/1997 | A61M/29/00 |
| WO | 9716217 | 5/1997 | A61M/25/10 |
| WO | 9741803 | 11/1997 | A61F/2/06 |
| WO | 9746174 | 12/1997 | A61F/2/06 |
| WO | 9819628 | 5/1998 | A61F/2/06 |
| WO | 9836709 | 8/1998 | A61F/2/06 |
| WO | 9837833 | 9/1998 | A61F/2/06 |
| WO | 9847446 | 10/1998 | A61F/2/06 |
| WO | 9847447 | 10/1998 | A61F/2/06 |
| WO | 9848879 | 11/1998 | A61M/25/00 |
| WO | 9853759 | 12/1998 | |
| WO | 9903426 | 1/1999 | A61F/2/06 |
| WO | 9903462 | 1/1999 | A61K/31/295 |
| WO | 9904726 | 2/1999 | A61F/2/06 |
| WO | 9913808 | 3/1999 | A61F/2/06 |
| WO | 99/15103 | 4/1999 | |
| WO | 9915108 | 4/1999 | A61F/2/06 |
| WO | 9915109 | 4/1999 | A61F/2/06 |
| WO | 9924104 | 5/1999 | A61M/25/10 |
| WO | 9934749 | 7/1999 | A61F/2/06 |
| WO | 99/36002 | 7/1999 | |
| WO | 9936002 | 7/1999 | A61F/2/06 |
| WO | 9936015 | 7/1999 | A61F/2/06 |
| WO | 9944539 | 9/1999 | A61F/2/06 |
| WO | 9956661 | 11/1999 | |
| WO | 9965419 | 12/1999 | A61F/2/06 |
| WO | 0007523 | 2/2000 | A61F/2/06 |
| WO | 0010485 | 3/2000 | A61F/2/06 |
| WO | 0010489 | 3/2000 | A61F/2/06 |
| WO | 0013613 | 3/2000 | A61F/2/06 |
| WO | 0016719 | 3/2000 | A61F/2/06 |
| WO | 0027307 | 5/2000 | A61F/2/06 |
| WO | 0027463 | 5/2000 | A61M/29/00 |
| WO | 0028922 | 5/2000 | A61F/2/06 |
| WO | 032266 | 6/2000 | A62M/25/10 |
| WO | 0145594 | 6/2000 | A61F/2/06 |
| WO | 0044307 | 8/2000 | A61F/2/06 |
| WO | 0044309 | 8/2000 | A61F/2/06 |
| WO | 0047134 | 8/2000 | A61F/2/06 |
| WO | 0048531 | 8/2000 | A61F/2/06 |
| WO | 0049951 | 8/2000 | A61B/17/11 |
| WO | 0051523 | 9/2000 | A61F/2/06 |
| WO | 0057813 | 10/2000 | A61F/2/06 |
| WO | 0067673 | 11/2000 | A61F/2/06 |
| WO | 0071055 | 11/2000 | A61F/2/06 |
| WO | 0074595 | 12/2000 | A61F/2/06 |
| WO | 0121095 | 3/2001 | A61F/2/06 |
| WO | 0121109 | 3/2001 | A61M/25/10 |
| WO | 0121244 | 5/2001 | A61M/25/00 |
| WO | 0130433 | 5/2001 | A61M/25/00 |
| WO | 0135715 | 5/2001 | |
| WO | 0135863 | 5/2001 | A61F/2/06 |
| WO | 0139697 | 6/2001 | A61F/2/06 |
| WO | 0141677 | 6/2001 | A61F/2/06 |
| WO | 0143665 | 6/2001 | A61F/2/06 |
| WO | 0143809 | 6/2001 | A61M/25/00 |
| WO | 0145785 | 6/2001 | A61M/25/00 |
| WO | 0149342 | 7/2001 | |
| WO | 0154621 | 8/2001 | A61F/2/06 |
| WO | 0154622 | 8/2001 | A61F/2/06 |
| WO | 0158385 | 8/2001 | A61F/2/06 |
| WO | 0160284 | 8/2001 | A61F/2/06 |
| WO | 0170294 | 9/2001 | A61L/31/08 |
| WO | 0170299 | 9/2001 | |
| WO | 0174273 | 10/2001 | A61F/2/06 |
| WO | 0189409 | 11/2001 | |
| WO | WO 02/39888 A2 | 5/2002 | |
| WO | WO 02/39926 A2 | 5/2002 | |

* cited by examiner

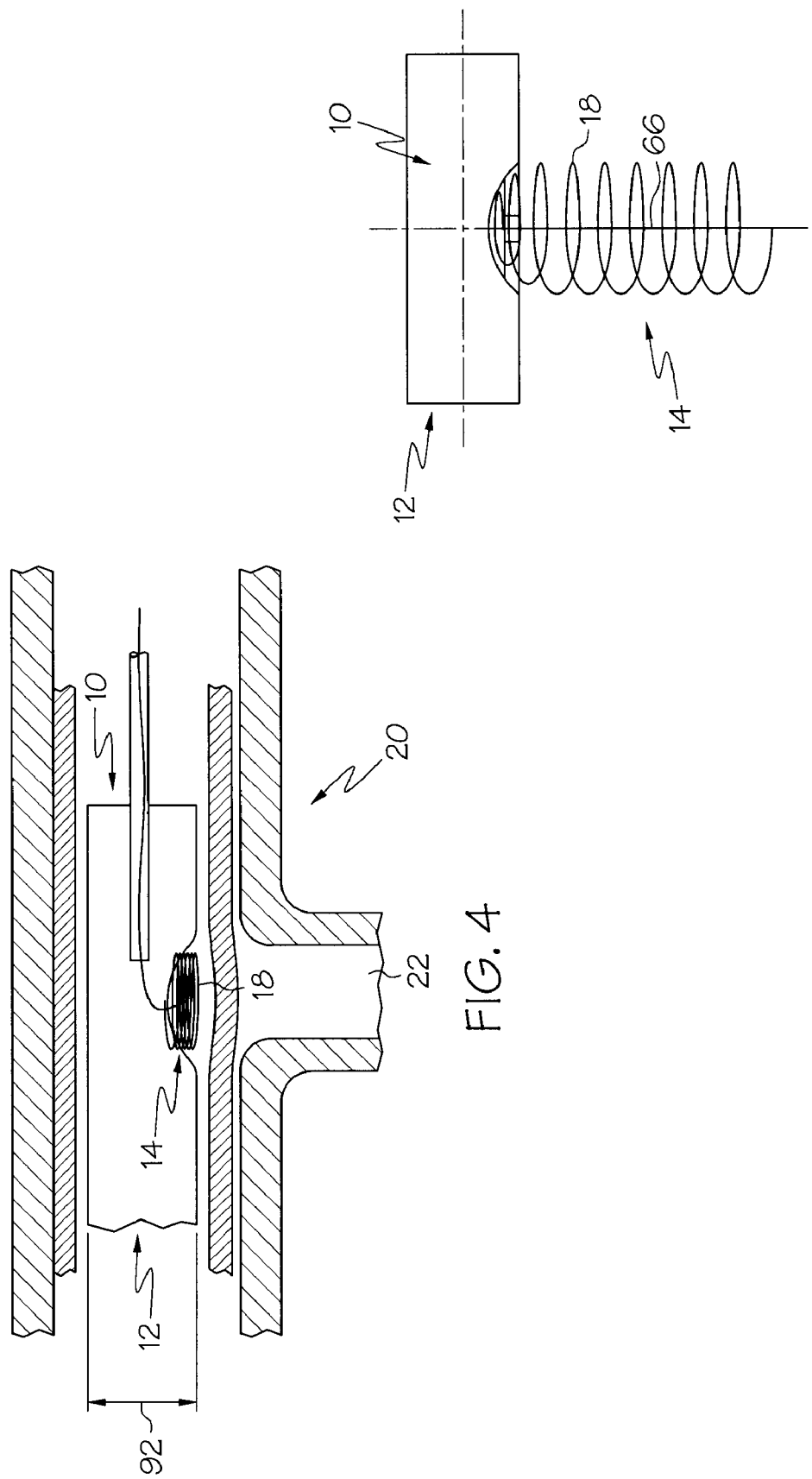

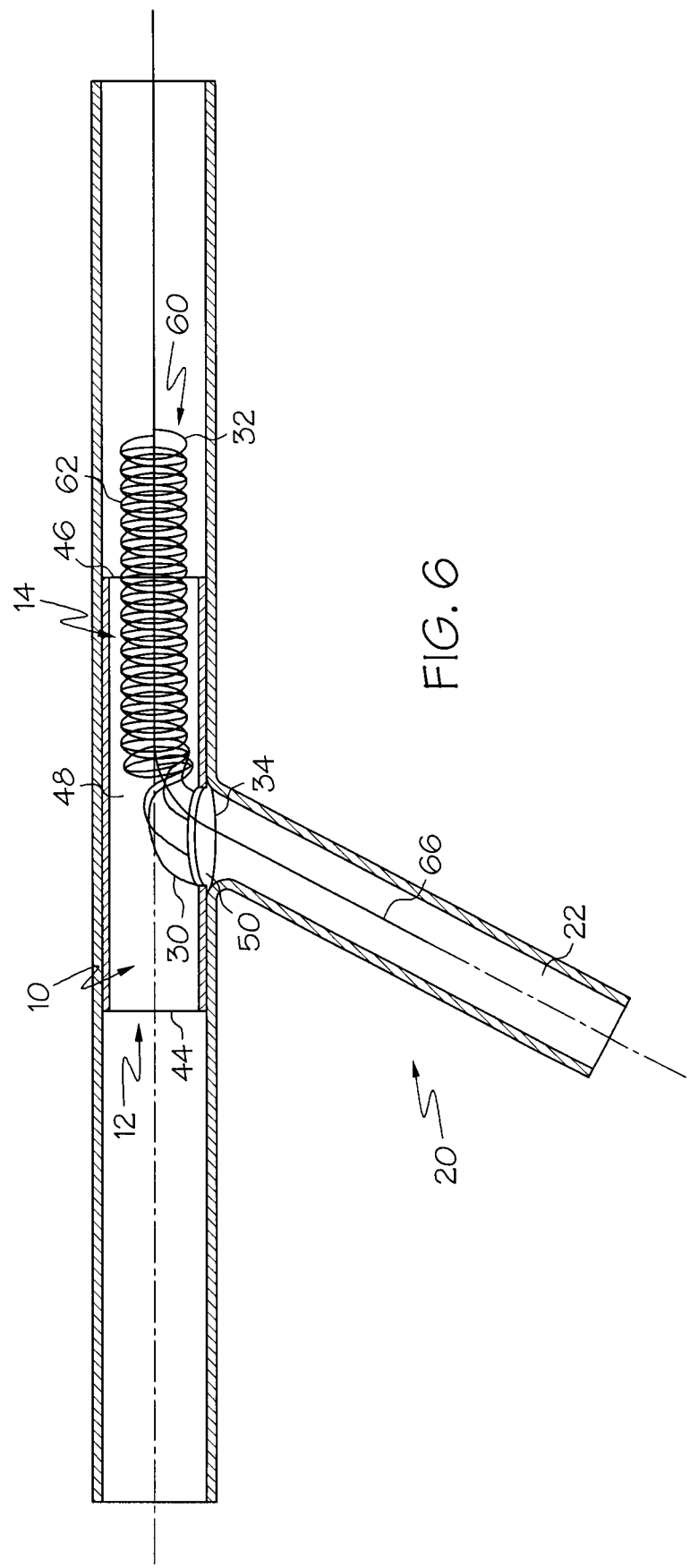

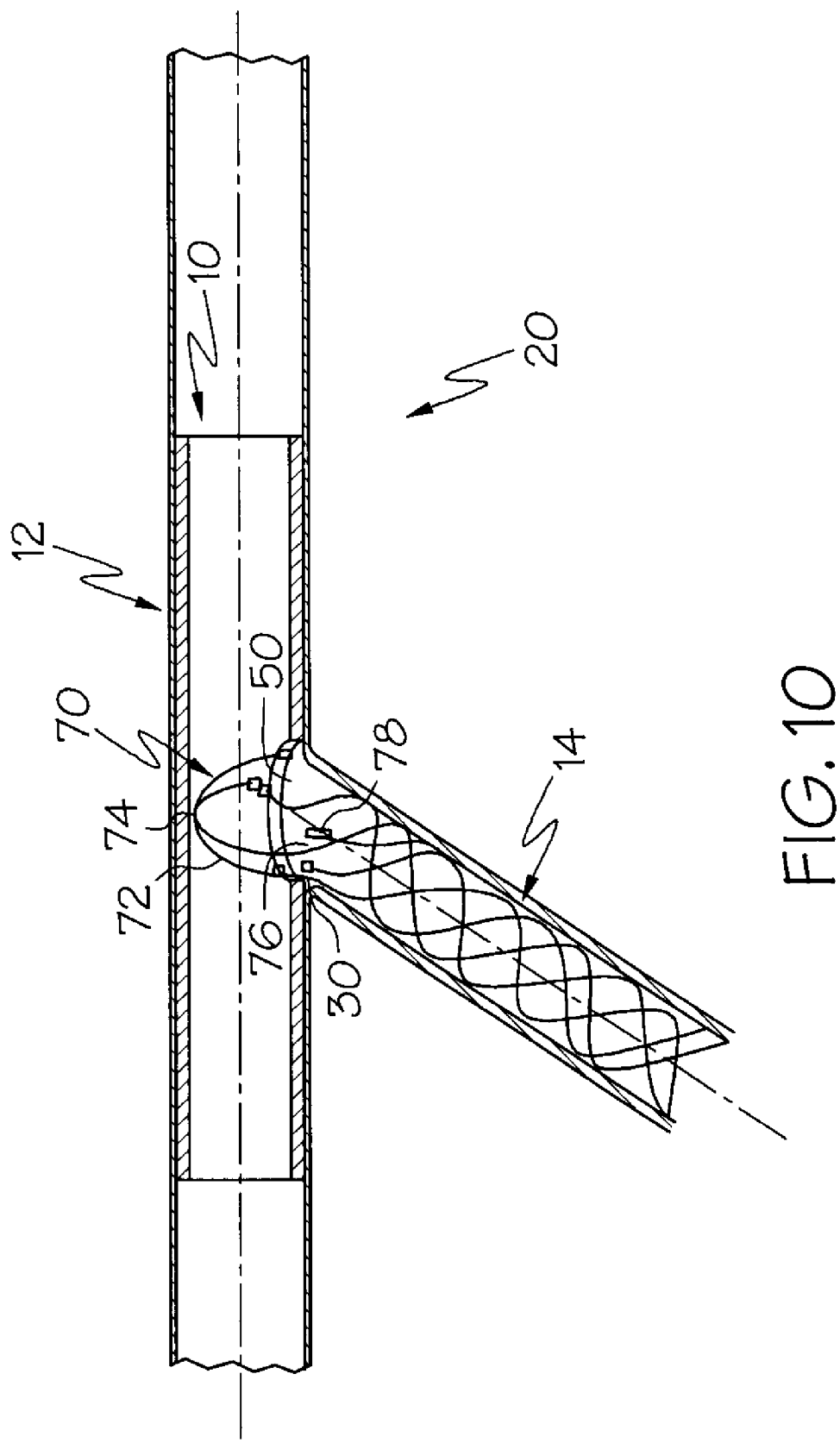

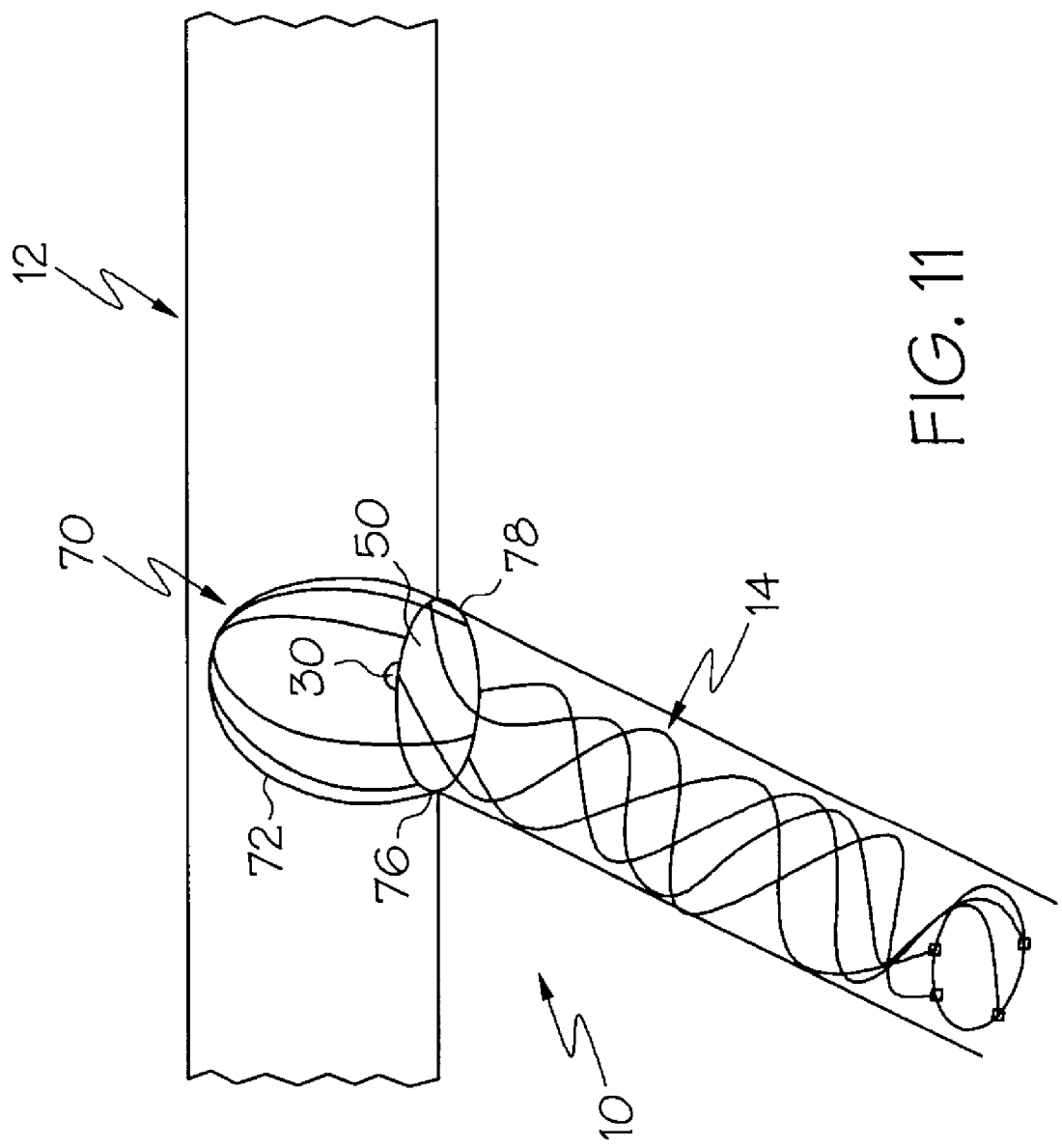

BIFURCATED STENT

CROSS-REFERENCE TO RELATED APPLICATIONS

This application claims priority from U.S. provisional applications 60/271,506 filed Feb. 26, 2001; U.S. provisional application 60/271,602 filed Feb. 26, 2001; and U.S. provisional application 60/271,595 filed Feb. 26, 2001; the entire content of each being incorporated herein by reference.

STATEMENT REGARDING FEDERALLY SPONSORED RESEARCH

Not Applicable

BACKGROUND OF THE INVENTION

Stents, grafts, stent-grafts, vena cava filters and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding or expanded by an internal radial force, such as when mounted on a balloon.

Stents are generally tubular devices for insertion into body lumens. Balloon expandable stents require mounting over a balloon, positioning, and inflation of the balloon to expand the stent radially outward. Self-expanding stents expand into place when unconstrained, without requiring assistance from a balloon. A self-expanding stent is biased so as to expand upon release from the delivery catheter. Some stents may be characterized as hybrid stents which have some characteristics of both self-expandable and balloon expandable stents.

A vessel having a stenosis may be viewed as an inwardly protruding arcuate addition of hardened material to a cylindrical vessel wall, where the stenosed region presents a somewhat rigid body attached along, and to, the elastic wall. The stenosis presents resistance to any expansion of the vessel in the region bridged by the stenosis. Stenoses vary in composition, for example, in the degree of calcification, and therefore vary in properties as well.

A stent may be used to provide a prosthetic intraluminal wall e.g. in the case of a stenosis to provide an unobstructed conduit for blood in the area of the stenosis. An endoluminal prosthesis comprises a stent which carries a prosthetic graft layer of fabric and is used e.g. to treat an aneurysm by removing the pressure on a weakened part of an artery so as to reduce the risk of embolism, or of the natural artery wall bursting. Typically, a stent or endoluminal prosthesis is implanted in a blood vessel at the site of a stenosis or aneurysm by so-called "minimally invasive techniques" in which the stent is compressed radially inwards and is delivered by a catheter to the site where it is required through the patient's skin or by a "cut down" technique in which the blood vessel concerned is exposed by minor surgical means. When the stent is positioned at the correct location, the catheter is withdrawn and the stent is caused or allowed to re-expand to a predetermined diameter in the vessel.

U.S. Pat. No. 4,886,062 discloses a vascular stent which comprises a length of sinuous or "zig-zag" wire formed into a helix; the helix defines a generally cylindrical wall which, in use, constitutes a prosthetic intraluminal wall. The sinuous configuration of the wire permits radial expansion and compression of the stent; U.S. Pat. No. 4,886,062 discloses that the stent can be delivered percutaneously and expanded in situ using a balloon catheter.

U.S. Pat. No. 4,733,665 discloses an expandable intraluminal graft which is constituted by a tubular member formed from a plurality of intersecting elongate members which permit radial expansion and compression of the stent.

EP-A-0556850 discloses an intraluminal stent which is constituted by a sinuous wire formed into a helix; juxtaposed apices of the wire are secured to one another so that each hoop of the helix is supported by its neighboring hoops to increase the overall strength of the stent and to minimize the risk of plaque herniation; in some embodiments the stent of EP-A-0556850 further comprises a tubular graft member to form an endoluminal prosthesis.

The devices cited above are generally satisfactory for the treatment of aneurysms, stenoses and other angeological diseases at sites in continuous unbifurcated portions of arteries or veins.

Within the vasculature however it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

For example, in the case of an abdominal aortic aneurysm ("AAA") in the infrarenal portion of the aorta which extends into one of the common iliac arteries, the use of one of the prior art prosthesis referred to above across the bifurcation into the one iliac artery will result in obstruction of the proximal end of the other common iliac artery; by-pass surgery is therefore required to connect the one iliac artery in juxtaposition with the distal end of the prosthesis to the other blocked iliac artery. It will be appreciated by a person skilled in the art that it is desirable to avoid surgery wherever possible; the requirement for by-pass surgery associated with the use of the prior art prosthesis in juxtaposition with a bifurcation in an artery therefore constitutes a significant disadvantage.

Another example of a vessel bifurcation is the left and right common carotid arteries. These arteries are the principal arteries of the head and neck. Both of the common carotid arteries are quite similar and divide at a carotid bifurcation or bulb into an external carotid artery and an internal carotid artery. In the region of the carotid bulb and the ostium of the internal carotid artery, stenoses present a particular problem for carotid stenting due to the large tapering of the vessel interior from the common carotid artery (both the left and the right) to the internal carotid artery. The region of the carotid bifurcation or bulb happens to be where stenoses most often occur, particularly in the region of the ostium to the internal carotid artery in both of the carotid arteries.

Embodiments of the present invention relate to endoluminal prosthesis (stents) that may be utilized in the region of a bifurcation of vessels. The present invention also embraces stent connecting means for connecting a stent (e.g. a stent which forms part of an endoluminal prosthesis or bifurcated stent) to another stent or portion thereof. Some embodiments of the invention are directed to designs of bifurcated stents and their method of manufacture, as well as apparatuses and methods for introducing prostheses to the vasculature and methods of treating angeological diseases.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention includes many different embodiments. At least one embodiment of the invention is directed to bifurcated stents and the methods of treating stenoses at a bifurcation site.

In some embodiments of the invention, the bifurcated stent includes at least one coiled member that defines at least one branch of the stent. In some embodiments the stent is characterized as having an expanding coil geometry. The expanding coil geometry provides at least one branch coil of the bifurcated stent with a larger diameter and/or a tighter coil pitch. In some embodiments of the invention, the portion of the stent that is deployed into the main branch includes a coil pitch that is greater than the pitch of adjacent stent coils. The at least one coiled member may be characterized as wire, ribbon or a combination thereof. Preferably, the wire coil will have an elliptical or round cross-section, whereas a ribbon may be characterized as a flattened wire coil. The wire ribbon or coil may be constructed from an etched panel of stent material or be manufactured from laser cut tubing.

In some embodiments where the coil is constructed from at least one ribbon, the ribbon may define a loose pitch coil or a tight pitch coil. In embodiments where the ribbon defines a tight pitch coil, the ribbon is preferably constructed of Nitinol and/or Elgiloy. In embodiments where the ribbon defines a coil, the coil may have a substantially helical configuration.

In some embodiments of the invention a stent may be a generally tubular body having one more openings with at least one coiled member engaged thereto. The coiled member may define at least one branch of the bifurcated stent. The coiled portion and the generally tubular body may have similar or different physical and/or performance characteristics. For example, the generally tubular body may define a balloon expandable primary portion of the bifurcated stent, whereas the coiled portion may define a self-expandable branch of the bifurcated stent that extends from the primary portion subsequent to expansion of the primary portion.

In at least one embodiment, the coiled portion has a collapsed state and a delivered state. In the collapsed state the coiled portion is collapsed in upon itself within the plane of the tubular wall the primary portion. In the delivered state, the coiled portion extends outwardly from the primary portion to a predetermined length.

In at least one embodiment of the invention a bifurcated stent comprises a primary portion having at least one branch portion. The branch portion is a woven mesh defined by at least one wire. The primary portion defines at least one opening through which the branch portion may be passed and engaged thereto. The branch portion is delivered through the primary portion in a collapsed inverted state and is expanded to a delivered state extending from the primary portion and in fluid communication therewith. Preferably, the woven mesh of the branch portion is constructed from Nitinol wire. In at least one embodiment, an end of the branch portion is welded to the area of the primary portion that defines the opening. Alternatively the wire of the branch portion is threaded through one or more flanges of the primary portion.

In at least one embodiment of the invention, the bifurcated stent includes one or more wire members which define a loop or loops within the interior of the primary section immediately adjacent to the opening through which a branch portion extends from. The loops preferably have a radius which is larger than the opening. The end of the branch portion immediately adjacent to the primary portion is engaged to one or more of the loops.

In at least one embodiment of the invention a bifurcated stent comprises a generally tubular primary portion which defines at least one side opening and two longitudinal openings. The bifurcated stent further comprises at least one coiled member which defines one or more side branches. Preferably, the at least one coiled member extends through the primary portion to provide a first coiled branch portion extending from the at least one side opening and a second coiled branch portion extending from at least one of the longitudinal openings. Preferably, the at least one coiled member is a wire and/or ribbon of Nitinol.

Additional details and/or embodiments of the invention are discussed below.

BRIEF DESCRIPTION OF THE SEVERAL VIEWS OF THE DRAWINGS

A detailed description of the invention is hereafter described with specific reference being made to the drawings.

FIG. 4 is a side view of an embodiment of the invention wherein the secondary branch is shown in the non-deployed state.

FIG. 5 is a side perspective view of the embodiment of the invention shown in FIG. 4 wherein the secondary branch is shown in the deployed state.

FIG. 6 is a side perspective view of an embodiment of the invention wherein a secondary branch of the bifurcated stent is shown in the collapsed inverted state prior to delivery.

FIG. 10 is a side perspective view of an embodiment of the invention.

FIG. 11 is a close up view of the wire loop retaining members and secondary branch of the embodiment shown in FIG. 10.

DETAILED DESCRIPTION OF THE INVENTION

Figure 1:
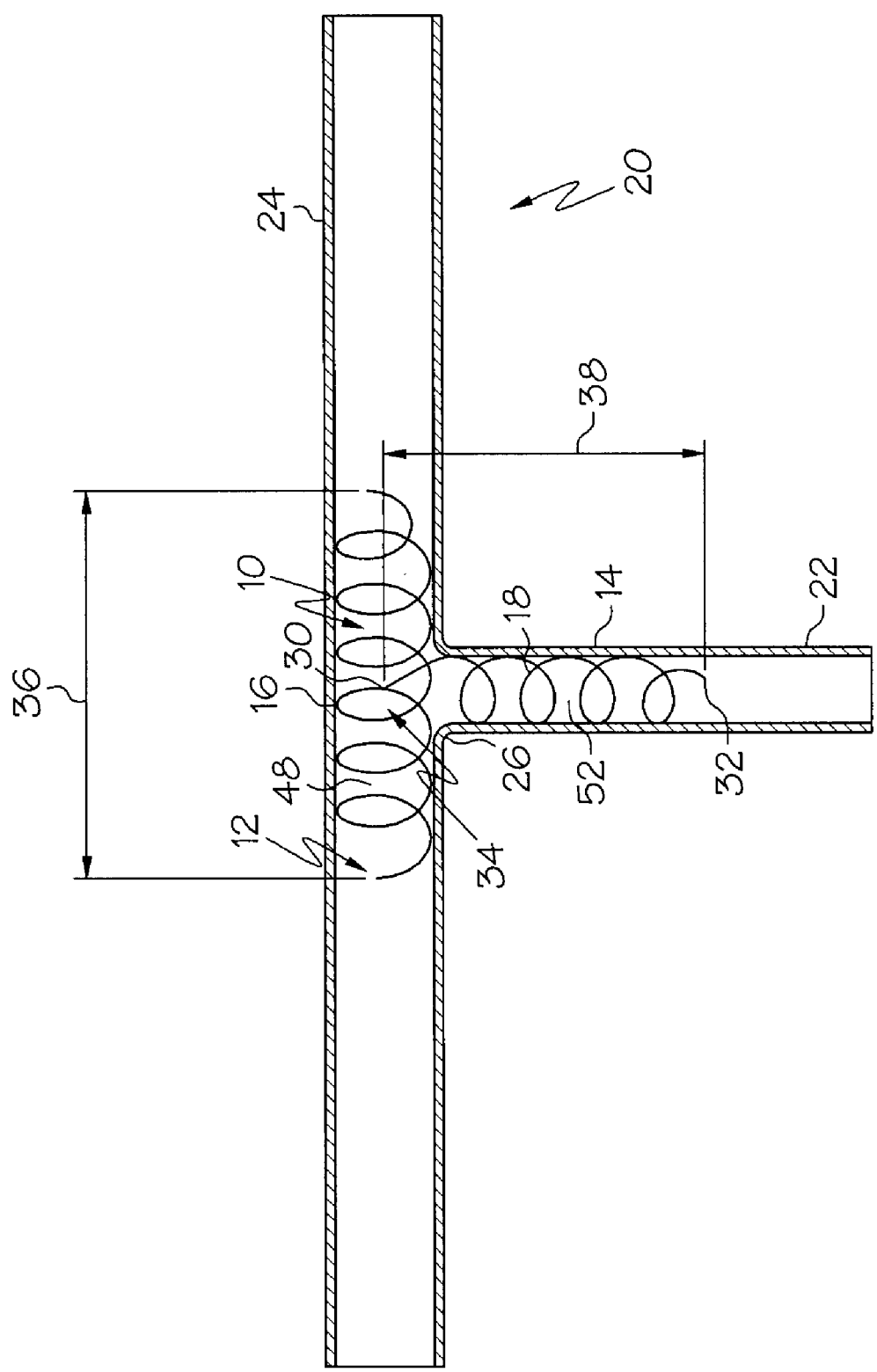
FIG. 1 is a side perspective view of an embodiment of the invention in the deployed state.

As indicated above the present invention includes many different embodiments. In some embodiments the invention is directed to various designs of bifurcated stents. In FIG. 1 an example of a bifurcated stent is shown wherein the bifurcated stent, shown generally at 10, is comprised of at least two stent portions 12 and 14. Portions 12 and 14 are preferably self-expanding coils or coil members 16 and 18 of wire.

In the present application the term "wire" refers to a pliable strand of elongated material which provides structural support. A wire may be characterized as having an elliptical or cylindrical cross-section, or having a more ribbon-like, flattened cross-section. Where the wire has a substantially round or circular cross-section, in some embodiments the wire has a diameter of about 0.002 to about 0.008 mm. Where a particular characteristic of the wire used to form coil 18 is noteworthy the relevant characteristics is noted and/or discussed in greater detail.

Where the stent portions 12 and 14 are self-expanding coils 16 and 18, the coils may be constructed from a shape memory metal such as nitinol or elgiloy or a shape memory polymer.

In the embodiment shown the stent 10 is delivered to a bifurcation 20 by a catheter or other delivery device (not shown). Once the stent is in position either portion 12 or 14 may be initially deployed. For example, when in the stent 10 is in position at the bifurcation 20, in one embodiment, the second stent portion 14 may be deployed into the daughter branch 22 of the bifurcation 20. Following deployment of the second stent portion 14, the first stent portion may be delivered into the primary branch 24 of the bifurcation and the delivery system withdrawn.

Second coil 18 has a first end 30 and a second end 32. In the embodiment shown in FIG. 1, the first end 30 is welded to a receiving region 34 of the first coil 16. It must be noted however, that welding the coils 16 and 18 together is merely one option for securing the stent portions 12 and 14 together. The present invention is also directed to embodiments where the coils 16 and 18 are integrally formed with a connection point therebetween, or where the coils 16 and 18 are joined in any other manner suitable for connecting stent portions 12 and 14 together.

When both coils 16 and 18 are deployed, such as is shown in FIG. 1, the first coil 16 defines a primary flow path 48 and the second coil defines a secondary flow path 52. The flow paths 48 and 52 are in fluid communication with each other.

In addition to the above, it should also be noted that the location of the receiving region 34 on the first coil 12 may be anywhere along the length of the first coil 12. As a result, end 30 of the second coil 14 may be engaged anywhere on the first coil 12. Such variable engagement position allows the bifurcated stent 10 to be produced for use in a wide range of bifurcation areas.

Not only may the relative position of the engagement between the first stent portion 12 and second stent portion 14 be made variable, so to may the relative lengths of the portions be varied. For example, the first portion 12 may have a length 36 different from or the same as the length 38 of the second portion 14. The range of values appropriate to lengths 36 and 38 are limited by the particular application and anatomical constrains.

Figure 2:
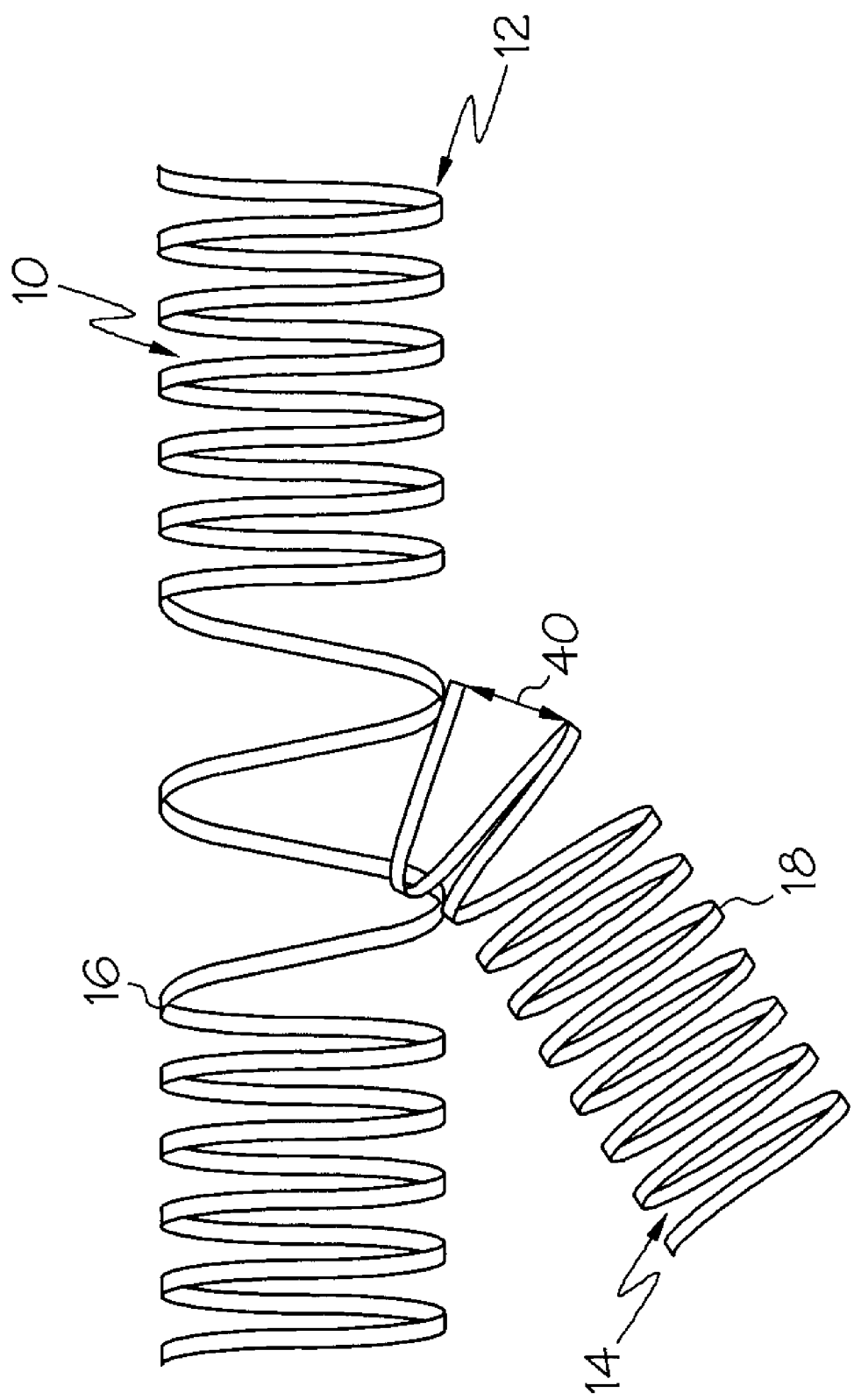
FIG. 2 is a side perspective view of an embodiment of the invention.

In order to provide stent support to the carina 26 the stent portions 12 and 14 may be provided with tighter or looser coil pitch as well as other different characteristics, such as diameter. For example, in one embodiment shown in FIG. 2, the first coil 16 has a diameter of approximately 4.0 mm, whereas the second coil 18 predominately has a diameter of approximately 3.0 mm. In addition, at least a portion 40 of the second coil 18 is provided with a larger diameter, relative to the rest of the coil 18. In the example shown in FIG. 2 the portion 40 has a diameter greater than about 3.0 mm. The larger diameter portion 40 of the coil 18 will extend toward the carina to provide for improved support and/or coverage of the region.

As indicated above, the portions 12 and 14 of the bifurcated stent 10 may have different physical properties, performance characteristics and be constructed from different materials from one another. In the embodiment shown in FIG. 3 for example, first stent portion 12 has a non-coiled configuration whereas the second stent portion 14 comprises a coil 18 such as described above. The non-coiled first portion 12, may be characterized as a tubular stent body 42 having a cellular design such as may be seen for example in the stents described in U.S. Pat. No. 6,348,065 and U.S. Pat. No. 6,013,091 the entire contents of each being incorporated herein by reference. Stent configurations other than those described in terms of a cellular configuration, such as for example the stents described in U.S. Pat. No. 6,033,433, the entire content of which is incorporated herein by reference, may also be used as the non-coiled portion of the bifurcated stent 10. In an alternative embodiment of the invention, the first portion 12 may be characterized as a substantially solid or porous tubular member.

Figure 3:
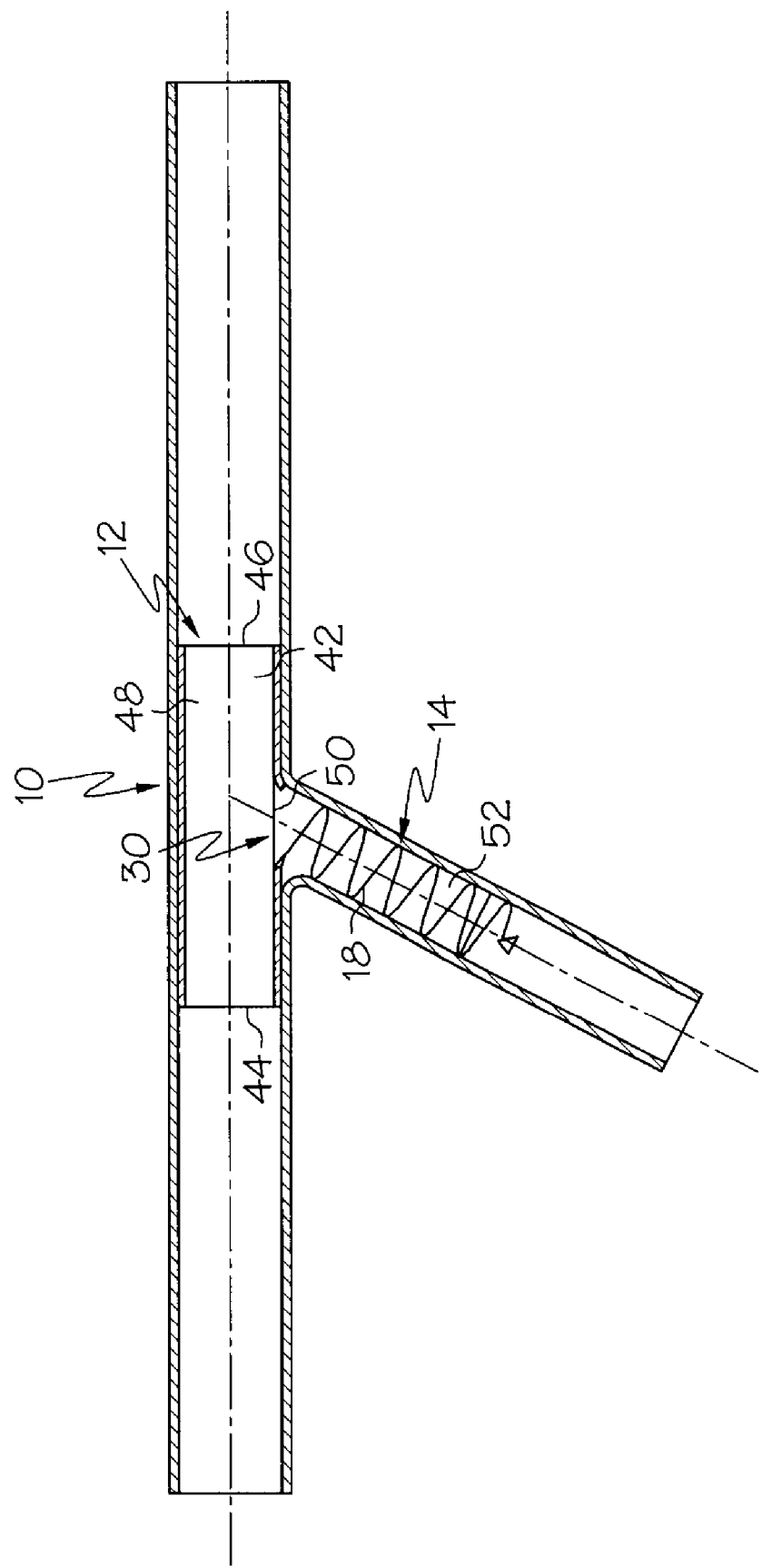
FIG. 3 is a side perspective view of an embodiment of the invention in the deployed state.

In the embodiment shown in FIG. 3 the body 42 of the first portion 12 defines a distal opening 44, a proximal opening 46 and a primary flow path 48 therebetween. The body 42 defines at least one secondary opening 50 which allows a secondary flow path 52 defined by the second portion 14 to be in fluid communication with the primary flow path 48.

The end 30 of the coil 18 may be engaged to any portion of the first portion adjacent to the secondary opening 50 by any manner desired. In at least one embodiment, end 30 of the second portion 14 is welded to a receiving region 34 of the first portion 12. The receiving region 34 may be located anywhere on the body 42 of the first portion 12.

The first portion 12 and the second portion 14 may function as, and may in fact be, distinct stent structures that are simply engaged together at the receiving region 34 to form the bifurcated stent 10. Either or both portions 12 and 14 maybe balloon expandable, self-expandable or may have hybrid stent features.

In some embodiments, where the second stent portion 14 defines a coil 18, such as shown in FIG. 3 above, a self-expandable coil 18 may tightly packaged into a predeployment collapsed configuration, such that prior to deployment the coil 18 is contained substantially within deployed first portion 12 and/or contained in the collapsed state adjacent thereto, such as is shown in FIG. 4. The tightness of the coil packaging and the characteristics of the delivery catheter 90 will determine the extent to which the coil 18 is contained internally or externally relative to the first portion 12. Preferably, prior to delivery of the second portion 14, the second portion 14 will not extend beyond the outer diameter 92 of the first portion 12.

As is shown in FIG. 5, following delivery of the first portion 12, the second portion 14 is allowed to self-expand into the secondary branch (shown in FIG. 4) as directed by the guide wire 66.

Figure 7:
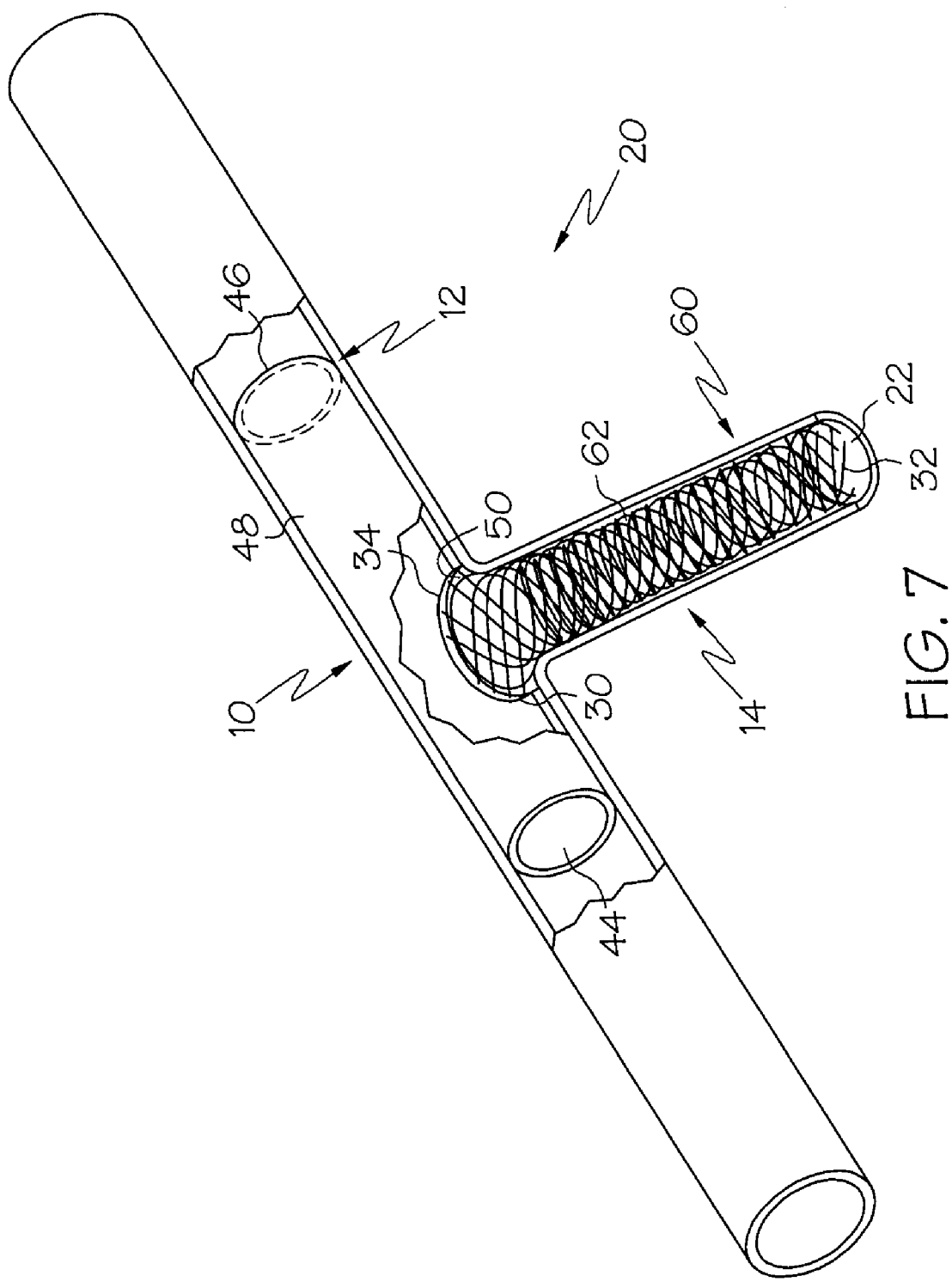
FIG. 7 is a perspective view of the embodiment shown in FIG. 6 wherein the secondary branch is shown in the delivered state.

In an alternative embodiment of the invention shown in FIGS. 6 and 7, the second portion 14 is a woven body 60 comprised of one or more fibers 62 rather than a single coil 18 as previously described. The individual fiber(s) 62 of the woven body 60 may be a wire or ribbon of appropriate stent material, such as nitinol. The woven body has a first end 30 and a second end 32. At first end 30 one or more fibers 62 are secured to the first portion 12 at one or more receiving regions 34 distributed about the secondary opening 50.

Figure 9:
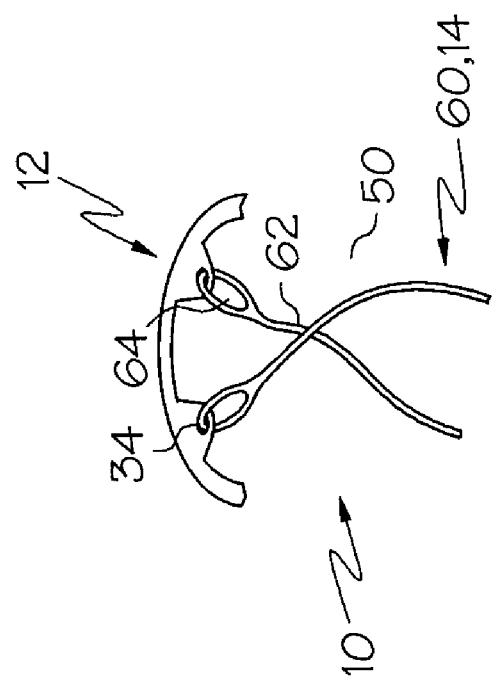
FIG. 9 is a close up view of a second optional interface between a primary branch and secondary branch such as may be used in the embodiments of FIGS. 6 and 7.
Figure 8:
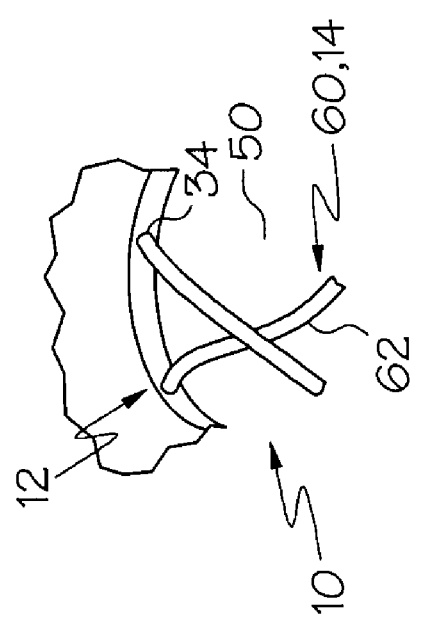
FIG. 8 is a close up view of a first optional interface between a primary branch and secondary branch such as may be used in the embodiments of FIGS. 6 and 7.

As is shown in the close-up partial view of the secondary opening 50 shown in FIG. 8, the fibers 62 may be welded to the receiving regions 34. Alternatively, in the embodiment shown in FIG. 9, the fibers 62 may have one or more loops or flanges 64 which are looped through or otherwise engaged to the receiving regions 34.

The woven body 60 of the second portion 14 has a unique configuration which allows it to be deployed from a collapsed state within the previously deployed first portion 12 shown in FIG. 6 to a fully deployed state shown in FIG. 7 where the second portion 14 is external and adjacent to the first portion 12.

As is shown in FIG. 6, prior to deployment, the collapsed body 60 is within the primary flow path 48 of the first portion 12. In some embodiments, the woven body 60 may extend out one of the proximal or distal openings 44 or 46 as shown. When the woven body 60 is deployed, the body 60 will self-expand inverting its shape as it passes through the secondary opening 50 and into the secondary branch 22. When the body 60 has fully inverted its configuration relative to the secondary opening 50 and fully expanded into the secondary opening 22, the second portion 14 of the stent 10 is fully deployed as shown in FIG. 7. In some embodiments it may be useful to retain a guide wire 66 at the bifurcation 20 in order to guide the inversion and expansion of the second portion 14 through the opening 50 and into the secondary branch 22.

In yet another embodiment of the invention shown in FIG. 10, the bifurcated stent 10 may be provided with a unique engagement mechanism between the first portion 12 and second portion 14 to provide for a wide range of articulation between the respective portions. In the embodiment shown in FIG. 10, the first portion 12 and second portion 14 may be have similar or different stent characteristics independent of each other. In at least one embodiment, the first portion 12 acts as a balloon expandable stent and the second portion 14 acts as a self-expandable stent. Preferably, the second portion 14 has a spiral or helical configuration similar to that of stents described in U.S. Pat. No. 6,042,597, the entire content of which is incorporated herein by reference.

The second portion 14 is engaged to the first portion 12 through a unique wire assembly 70 which acts to moveably engage the end 30 of the second portion 14 to the secondary opening 50 of the first portion 12.

Wire assembly 70 is comprised of one or more wire or ribbon members 72 which are disposed within or about the first portion 12 adjacent to the secondary opening 50. In some embodiments a plurality of members 72 converge and are engaged to the first portion at one or more primary engagement points 74. The ends 76 of each member 72 extend toward the secondary opening 50 where they are each engaged to a secondary engagement surface 78 located at or around end 30 of the second portion 14. In some embodiments the ends 76 may also be engaged to portions of the first portion 12 adjacent to the secondary opening 50 at secondary engagement surfaces 78.

In the embodiment shown in FIG. 11, the members 72 are constructed and arranged to provide a wire assembly 70 that has a diameter larger than that of the secondary opening 50. Wire assembly 70 is engaged to the end 30 of the second portion 14 as described above. However, the wire assembly is only frictionally engaged to the first portion 12 where the members 72 contact the area of the first portion 12 that defines the secondary opening 50. This type of engagement provides the secondary portion 14 with a rotatable ball-joint type connection to the first portion 12 thereby providing the second portion with a relatively large degree of articulation relative to the first portion 12.

In the various embodiments of the invention discussed thus far, a bifurcated stent 10 may include a first portion 12 and a second portion 14 such as has been previously described. However, in the embodiment shown in FIG. 12 it is shown that the invention is also directed to a bifurcated stent 10 having a third portion 15 as well.

Figure 12:
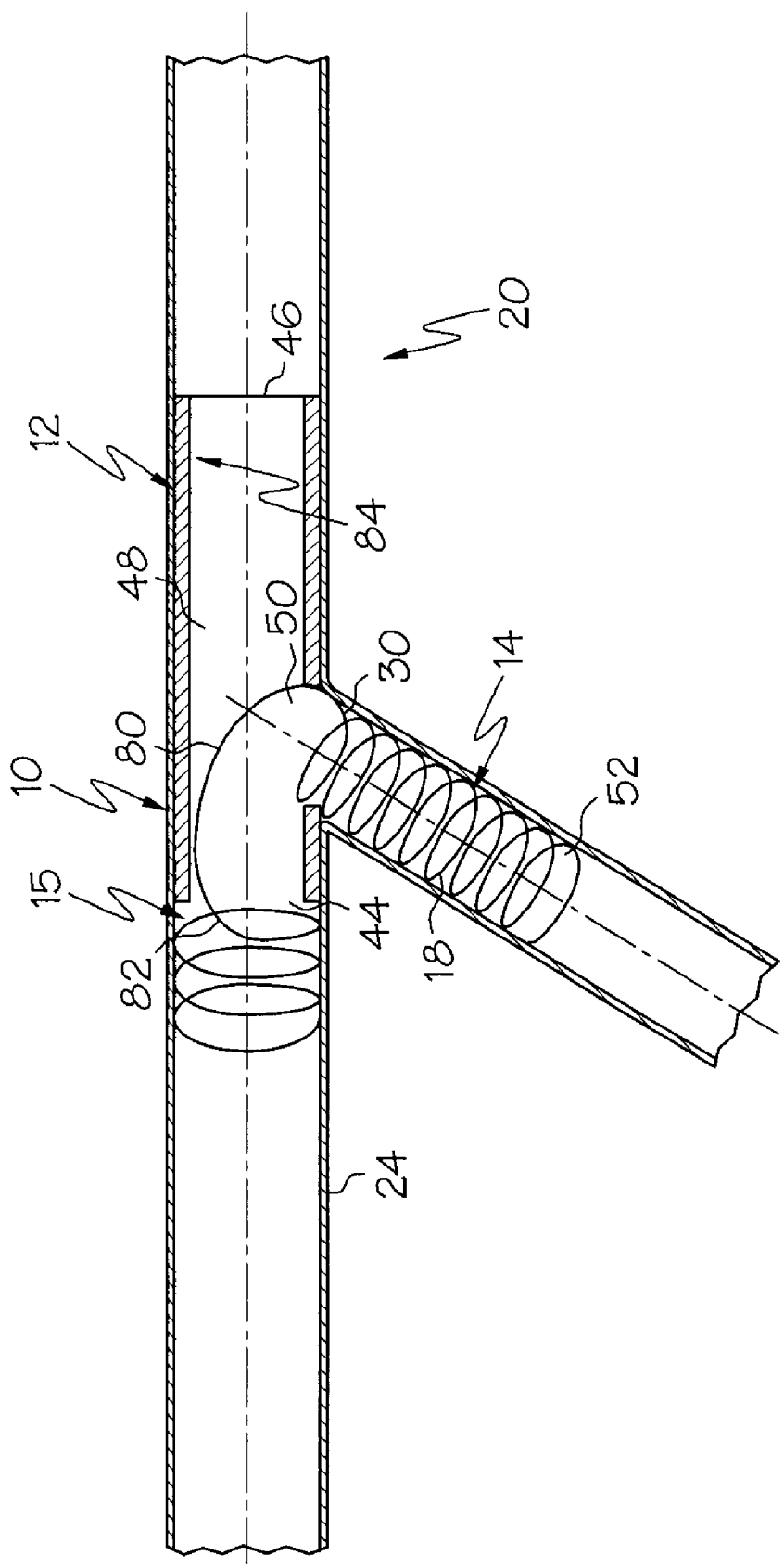
FIG. 12 is a side perspective view of an embodiment of the invention wherein a coiled portion of a bifurcated stent extends outward from two openings of a primary stent section.

In the embodiment shown in FIG. 12, the first portion 12 is preferably a non-coiled stent such as previously described in relation to FIG. 3. The first portion 12 may be any type of stent design, however in at least one embodiment the first portion 12 acts as a balloon-expandable stent. In contrast to the first portion 12, the second and third portions 14 and 15 are characterized as a single self-expanding coil 18 that defines each portion 14 and 15. Coil 18 is preferably constructed of nitinol wire. A portion 80 of the coil 18 connects the second portion 14 to the third portion 15 by extending from the end 30 of the second portion 14 to the end 82 of the third portion 15. The portion 80 of the coil that connects the two portions 14 and 15 together passes from the secondary opening 50 to one of the proximal or distal openings 44 or 46 through the primary flow passage 48 of the first portion 12.

In the deployed state shown in FIG. 12, the second portion 14 extends radially away from the first portion 12 to provide a secondary flow path 52 that is in fluid communication with the primary flow path 48 via opening 50. In the deployed state the third portion 15, extends longitudinally from opening 44, or optionally opening 46, thereby extending the primary flow path 48 and stent support further into vessel 24.

Portion 80 frictionally engages the interior 84 of the first portion 12 thereby coupling the second and third portions 14 and 15 to the first portion 12 without welds or other relatively rigid engagement mechanisms.

Figure 13:
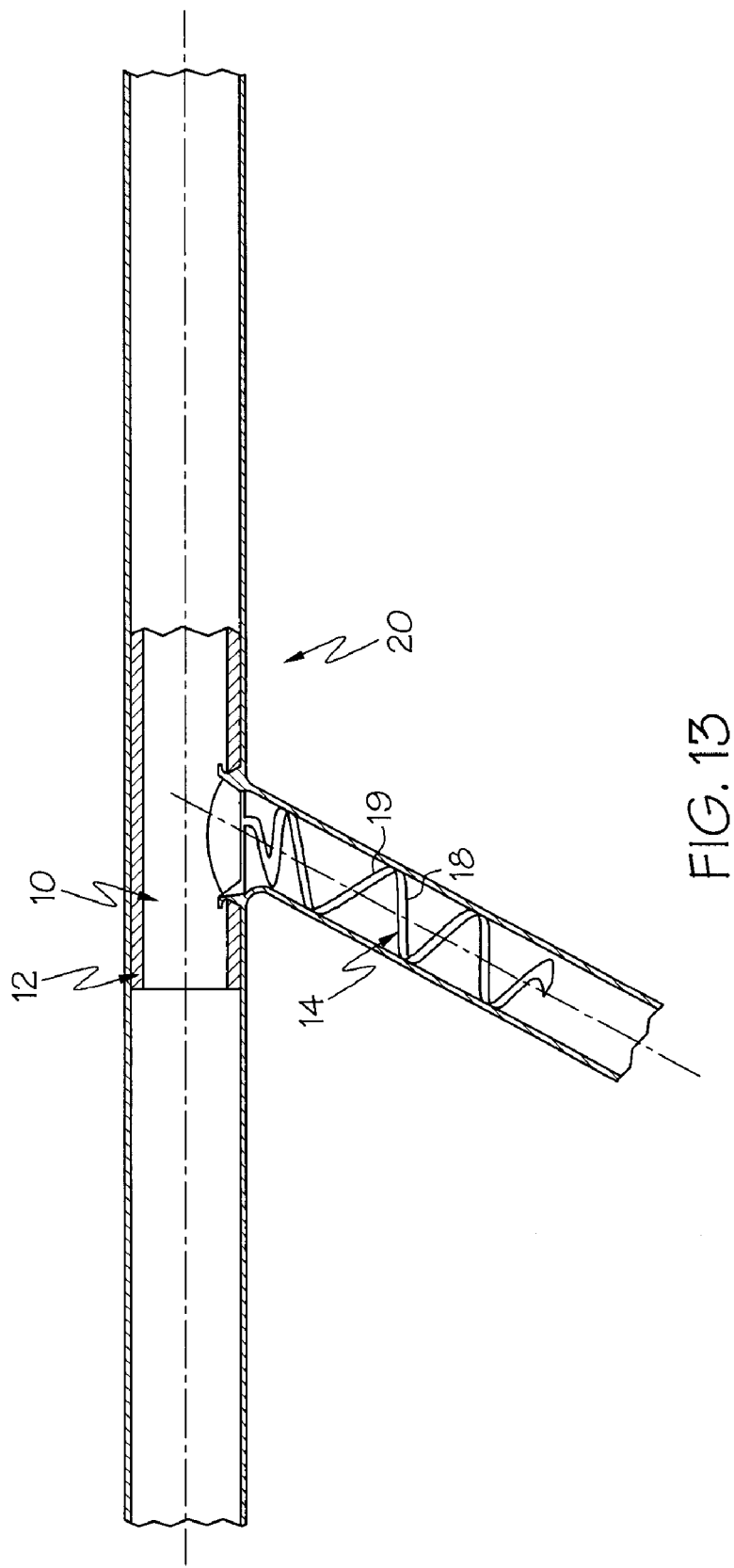
FIG. 13 is a side perspective view of an embodiment of the invention.
Figure 14:
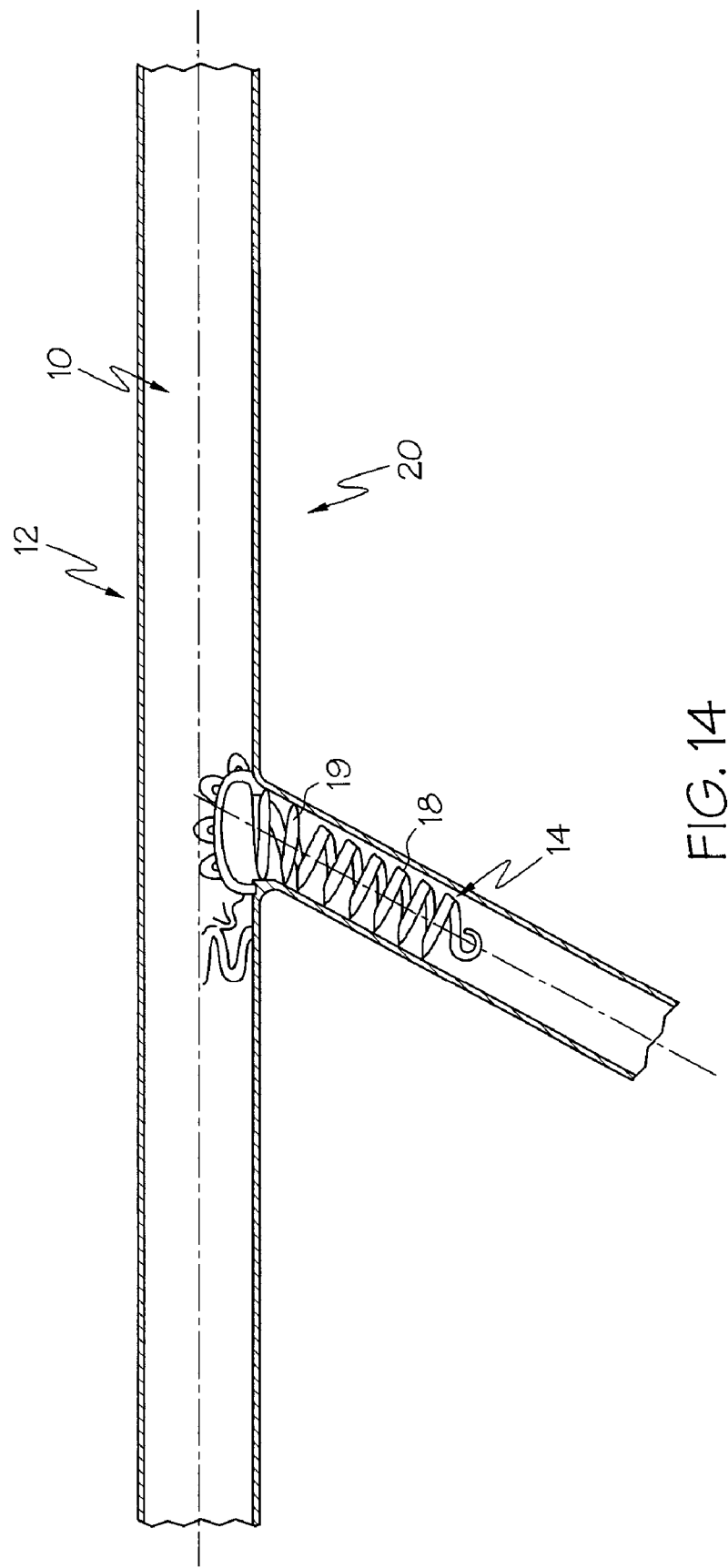
FIG. 14 is a side perspective view of an embodiment of the invention.
Figure 15:
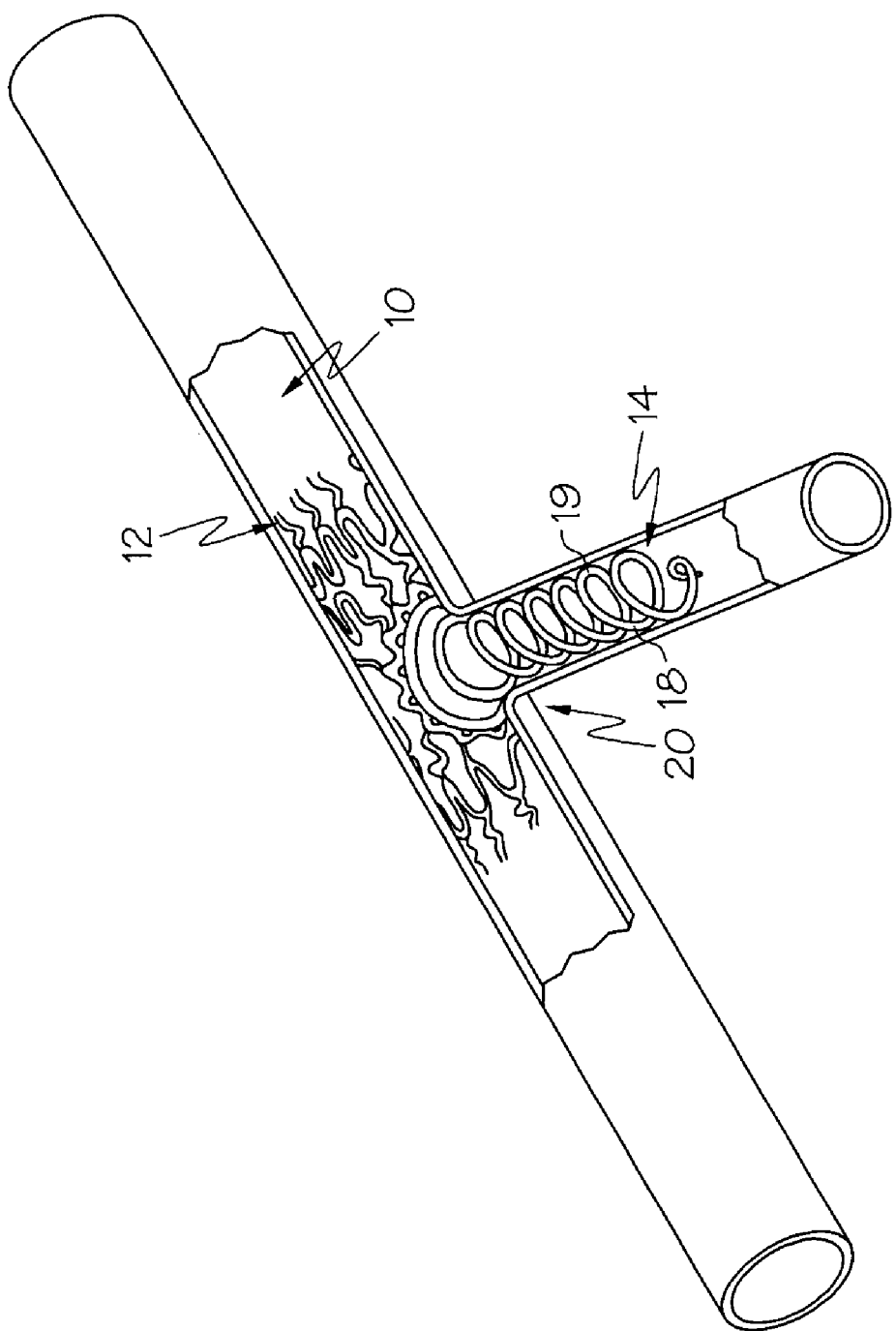
FIG. 15 is a cut-away perspective view of the embodiment shown in FIG. 14 shown deployed at a bifurcation site.

As indicated above the various bifurcated stent designs discussed thus far may include second portions 14 and/or first portions 12 that are constructed from a coil 18 of nitinol or other shape-memory wire or ribbon. In the embodiments shown in FIGS. 13–15 the bifurcated stent 10 is clearly shown having a coil 18 constructed from a ribbon 19. In the embodiments shown in FIGS. 13–15 the first portion 12 is preferably a substantially tubular stent body having a non-coiled configuration such as described above in the description of FIG. 3. In the various embodiments shown in FIGS. 13–15 the diameter and pitch of the coil 18 may be varied. Similarly, the engagement between the first portion 12 and the second portion 14 may likewise be provided for by any of the methods or mechanisms described above or that are otherwise known. In some embodiments, the first portion 12 and second portion 14 may be integrally formed with ribbon 19 may be an extension of the first portion 12.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

What is claimed is:

1. A bifurcated stent comprising:
    a first stent section, the first stent section comprising a substantially tubular body defining openings at both ends, the substantially tubular body comprising a receiving region, the receiving region of the substantially tubular body defining a secondary opening between the openings at the ends of the tubular body, the first section being expandable from a predeployed state to a deployed state, in the deployed state the first stent section defining a primary flow path, in the deployed state the first section defines an outer diameter; and
    a second stent section, the second stent section constructed from at least one member of the group consisting of a coil of wire having a substantially circular cross-section, a flattened ribbon, an etched panel, laser cut tubing and any combination thereof, the second stent section being expandable from a predeployed state to a deployed state, the second stent section having an end engaged to the receiving region of the first stent section, in the deployed state the second stent section defining a secondary flow path, the secondary flow path in fluid communication with the primary flow path, the first stent section and the second stent section being expandable independently from one another, at least a portion of at least one of the first stent section and the second stent section being constructed from a wire member, when the first section is in the deployed state and the second section is in the predeployed state, the second section has a length that does not extend substantially beyond the outer diameter of the first section.

2. The bifurcated stent of claim 1 wherein the first stent section is constructed from at least one member of the group consisting of a coil of wire having a substantially circular cross-section, a flattened ribbon, an etched panel, laser cut tubing and any combination thereof.

3. The bifurcated stent of claim 2 wherein the second stent section is constructed from the coil of wire, the coil of wire defining a first diameter and a second diameter.

4. The bifurcated stent of claim 1 wherein in the deployed state the first section defines an outer diameter, when the first section is in the deployed state and the second section is in the predeployed state, the second section is substantially contained within the primary flow path defined by the first section.

5. The bifurcated stent of claim 1 wherein the first stent section is balloon expandable and the second stent section is self-expandable.

6. The bifurcated stent of claim 1 wherein at least one of the first stent section and the second stent section are self-expandable.

7. The bifurcated stent of claim 1 wherein at least one of the first stent section and the second stent section are balloon-expandable.

8. The bifurcated stent of claim 1 wherein the wire is characterized as a flattened ribbon.

9. The bifurcated stent of claim 1 wherein the second stent section comprises a wire mesh.

10. The bifurcated stent of claim 9 wherein the wire mesh comprises a plurality of woven wires.

11. The bifurcated stent of claim 10 wherein receiving region comprises a plurality of the engagement points, the woven wires having ends, at least some of the ends being engaged to the engagement points.

12. The bifurcated stent of claim 11 wherein the at least some of the ends are welded to the engagement points.

13. The bifurcated stent of claim 11 wherein the at least some of the ends comprise a looped flange, each looped flange being moveably engaged to one of the engagement points.

14. The bifurcated stent of claim 1 wherein in the predeployed state the second stent section extends from the receiving region into the primary flow path defined by the first stent section.

15. The bifurcated stent of claim 14 wherein in the deployed state the second stent section extends from the receiving region and radially outward from the first stent section, the second stent section constructed and arranged being constructed and arranged such that when the second stent section is expanded from the predeployed state to the deployed state the position of the second stent section is inverted relative to the secondary opening.

16. A bifurcated stent comprising:
    a substantially tubular stent body being expandable from a predeployed state to a deployed state, the substantially tabular stent body having openings at both ends and in the deployed state defining a primary flow path therethrough, the substantially tubular body further defining a secondary opening, the secondary opening having an opening diameter;

a secondary stent body, the secondary stent body being expandable from a predeployed state to a deployed state independently of the substantially tubular stent body, the secondary stent body having openings at both ends and in the deployed state defining a secondary flow path therethrough, one end of the secondary stent body being immediately adjacent to the secondary opening of the substantially tubular stent body; and a wire engagement apparatus, the wire engagement apparatus comprising at least one wire member, at least a first portion of the at least one wire member being moveably engaged to the substantially tubular stent body, the at least a first portion of the wire engagement apparatus defining a ball of a ball-joint connection wherein the secondary opening of the substantially tubular stent body defines the joint, at least a second portion of the at least one wire member being engaged to the end of the secondary stent body being immediately adjacent to the secondary opening of the substantially tubular stent body, the secondary stent body being moveable relative to the substantially tubular stent body.

17. The bifurcated stent of claim 16 wherein the secondary stent body is constructed at least partially from wire.

18. The bifurcated stent of claim 17 wherein the secondary stent body is constructed at least partially from a shape memory material.

19. The bifurcated stent of claim 17 wherein the secondary stent body is self-expandable.

20. The bifurcated stent of claim 16 wherein the wire engagement apparatus is substantially contained within the primary flow path of the substantially tubular body adjacent to the secondary opening.

21. The bifurcated stent of claim 20 wherein the at least one wire member is shaped to define an apparatus diameter, the apparatus diameter being larger than the opening diameter.

22. The bifurcated stent of claim 16 wherein the wire engagement apparatus is disposed about a portion of the substantially tubular body.

23. A bifurcated stent comprising:

a substantially tubular stent body being expandable from a predeployed state to a deployed state, the substantially tabular stent body having a proximal end and a distal end, the substantially tubular stent body defining a flow path opening at each end and in the deployed state defining a primary flow path therethrough, the substantially tubular body further defining a secondary opening between the openings at each end of the substantially tubular stent body; and a secondary stent body, the secondary stent body comprising a wire member, the wire member defining a first coiled portion, a second coiled portion and connection portion therebetween, the secondary stent body being expandable from a predeployed state to a deployed state independently of the substantially tubular stent body, in the deployed state the first coiled portion being positioned immediately adjacent to the secondary opening of the substantially tubular stent body and extending radially therefrom, in the deployed state the second coiled portion being positioned immediately adjacent to one of the flow path openings of the substantially tubular stent body and extending longitudinally therefrom, the connection portion being fictionally engaged to the substantially tubular stent body.

* * * * *